US005939396A

United States Patent [19]

Hellerqvist

[11] Patent Number: 5,939,396

[45] Date of Patent: Aug. 17, 1999

[54] METHOD FOR PURIFYING GBS TOXIN/ CM101

[75] Inventor: Carl G. Hellerqvist, Brentwood, Tenn.

[73] Assignee: Vanderbilt University, Nashville, Tenn.

[21] Appl. No.: 09/028,972

[22] Filed: Feb. 24, 1998

Related U.S. Application Data

[62] Division of application No. 08/744,770, Sep. 30, 1996, Pat. No. 5,311,403.

[51] Int. Cl.[6] .......... A01N 43/04; C12P 21/04; C12N 1/20; C07J 3/00

[52] U.S. Cl. .......... 514/23; 435/72; 435/253.4; 536/6

[58] Field of Search .......... 435/72, 73, 253.4; 514/23, 25, 42, 43, 54, 57, 60; 530/412, 414, 415, 416; 536/6

[56] References Cited

U.S. PATENT DOCUMENTS

| | | | |
|---|---|---|---|
| 4,242,326 | 12/1980 | Sugawara et al. | 424/116 |
| 4,421,650 | 12/1983 | Nagasawa et al. | 210/635 |
| 4,771,128 | 9/1988 | Ferris et al. | 530/391.7 |
| 4,882,317 | 11/1989 | Marburg et al. | 514/54 |
| 5,010,062 | 4/1991 | Hellerqvist | 514/54 |
| 5,059,654 | 10/1991 | Hou et al. | 525/54.1 |
| 5,094,960 | 3/1992 | Bonomo | 436/178 |
| 5,225,331 | 7/1993 | Jennings et al. | 435/7.34 |
| 5,302,386 | 4/1994 | Kasper et al. | 424/197.11 |

FOREIGN PATENT DOCUMENTS

| | | |
|---|---|---|
| 0 445 280 B1 | 9/1991 | European Pat. Off. . |
| WO 93/19096 | 9/1993 | WIPO . |

OTHER PUBLICATIONS

El Rassi Z, "Recent progress in reversed–phase and hydrophobic interaction chromatography of carbohydrate species," *Journal of Chromatography A*, vol. 720 (1):93–118 (1996).

Hellerqvist, C.G. et al., "Studies on group B β–hemolytic streptococcus I. Isolation and partial characterization of an extra–cellular toxin," *Pediatr. Res.*, 15:892–898 (1981).

Hellerqvist, C. et al., "Molecular basis for group B β–hemolytic streptococcal disease," Proc. Natl. Acad. Sci. USA, vol. 84:51–55 (1987).

Hellerqvist, C.G., et al., "Anti–tumor effects of GBS toxin: a polysaccharide exotoxin from group B β–hemolytic streptococcus," *J. Canc Res. Clin. Oncol.*, 120:63–70 (1993).

Hellerqvist, C.G. et al., "Preliminary results of a phase I trial of CM101 in cancer patients," *Journal of Cellular Biochemistry*, vol. 19B:26 (1995).

Jennings, H. J. et al., "Structural Determination and Serology of the Native Polysaccharide Antigen of Type–III Group β–Streptococcus," *Canadian J. of Biochem.*, vol. 58 (2):112–120 (1980).

Michon, F., "Multiantennary group–specific polysaccharide of Group B Streptococcus," *Biochem.*, 27:5341–51 (1988).

Paoletti, L.C. et al., "Neonatal mouse protection against infection with multiple group B streptococcal (GBS) serotypes by maternal immunization with a tetravalent GBS polysaccharide–tetanus toxoid conjugate vaccine," *Infect. Immun.*, 62 (8):3236–43 (1994).

Schoel, B. et al., "Hydrophobic interaction chromatography for the purification of cytolytic bacterial toxins," Journal of Chromatography A, vol. 667:131–139 (1994).

*Primary Examiner*—Jean C. Witz
*Assistant Examiner*—Susan Hanley
*Attorney, Agent, or Firm*—Cooley Godward LLP

[57] ABSTRACT

A method for purifying a polysaccharide from group B β-hemolytic Streptococcus (GBS) bacteria includes contacting a bacterial fermentation stock with a hydrophobic interaction chromatography (HIC) resin. Additional steps may include a phenol/saline extraction and an ion exchange chromatography. The method results in a product having very high purity. The product of the purification provides a composition which is highly useful in both research and therapeutic settings.

21 Claims, 14 Drawing Sheets

IL-6 activity profile of fractions obtained from 10K5P6 concentrate run on 100ml Butyl Sepharose (FT = flow-through: IM = IM phosphate fraction; 0.25M = 0.25M phosphate fraction; $H_2O$ = water fraction; EtOH = ethanol fraction).

| PK. Num | Ret Time | Component Name | Concentration pmol/ul | Height | Area | Bl. Code | % Delta |
|---|---|---|---|---|---|---|---|
| 1 | 1.58 | | 0.000 | 36832 | 563550 | 1 | |
| 2 | 3.25 | | 0.000 | 1869 | 120205 | 1 | |
| 3 | 5.42 | | 0.000 | 43126 | 510460 | 1 | |
| 4 | 10.67 | Gal-N | 2.029 | 30358 | 761900 | 1 | -0.03 |
| 5 | 12.58 | Glc-N | 2.135 | 25737 | 718738 | 2 | 0.67 |
| 6 | 14.08 | Gal | 5.363 | 59697 | 1781642 | 2 | 0.60 |
| 7 | 15.17 | Glu | 2.417 | 30036 | 887398 | 2 | 0.57 |
| 8 | 16.17 | Man | 2.286 | 15296 | 581897 | 2 | 0.54 |
| 9 | 19.83 | | 0.000 | 1254 | 50613 | 1 | |
| 10 | 24.42 | | 0.000 | 894 | 23565 | 1 | |
| | | Totals | 14.229 | 245098 | 5999967 | | |

| PK. Num | Ret Time | Component Name | Concentration pmol/ul | Height | Area | Bl. Code | % Delta |
|---|---|---|---|---|---|---|---|
| 1 | 1.58 | | 0.000 | 8497 | 205165 | 1 | |
| 2 | 5.33 | | 0.000 | 28988 | 380255 | 1 | |
| 3 | 10.50 | Gal-N | 0.895 | 15216 | 400665 | 1 | 0.77 |
| 4 | 12.42 | Glc-N | 0.783 | 10964 | 310639 | 2 | 1.36 |
| 5 | 13.67 | Gal | 2.461 | 34184 | 981936 | 2 | -1.18 |
| 6 | 14.83 | Glu | 1.013 | 11919 | 368215 | 2 | -1.11 |
| 7 | 15.92 | Man | 0.711 | 4252 | 221879 | 2 | 3.83 |
| 8 | 23.75 | | 0.000 | 1781 | 87055 | 1 | |
| | | Totals | 5.864 | 115801 | 2955809 | | |

METHOD FOR PURIFYING GBS TOXIN/CM101

CROSS-REFERENCE TO RELATED APPLICATION

This application is a Divisional of U.S. Ser. No. 08/744,770, filed Sep. 30, 1996 and issued as U.S. Pat. No. 5,811,403 on Sep. 22, 1998.

INTRODUCTION

1. Technical Field

This invention relates to improved methods of purification for a polysaccharide.

2. Background

CM101, a GBS toxin, is a pathogenic molecule isolated from group B β-hemolytic Streptococcus (GBS) bacteria. Newborn infants may become infected with GBS, a condition known as GBS pneumonia or "early-onset disease," and suffer from sepsis, granulocytopenia, and respiratory distress, i.e. pulmonary hypertension and proteinaceous pulmonary edema (Hellerqvist, C. G. et al., *Studies on group B β-hemolytic streptococcus I. Isolation and partial characterization of an extra-cellular toxin., Pediatr. Res.*, 15:892–898 (1981)).

Despite the harmful effects to neonates exposed to GBS, CM101 is not known to cause toxicity in older humans. In fact, research into this toxin has revealed a significant therapeutic application. See U.S. Pat. No. 5,010,062 and Hellerqvist, C. G. et al., *Early Results of a Phase I Trial of CM*101 *in Cancer Patients., Proceedings of the American Association of Cancer Research Annual Meeting* (1995), wherein CM101 is utilized to inhibit vascularization of tumors. Obtaining purified CM101 is critical, therefore, for both research and therapeutic purposes.

CM101 is a complex polysaccharide toxin having a molecular weight of approximately 300,000 Daltons and comprising N-acetyl-galactosamine, N-acetyl-glucosamine, glucose, galactose, and mannose residues. Carboxylic acid residues are also believed to be an integral part of the molecule. Repeating active epitopes most likely play an important role in the pathophysiological response to CM101 by crosslinking receptors on target endothelium (Hellerqvist, C. G. et al., *Early Results of a Phase I Trial of CM*101 *in Cancer Patients., Proceedings of the American Association of Cancer Research Annual Meeting* (1995)).

U.S. Pat. No. 5,010,062 provides a method of purification of a GBS toxin. The method taught is labor-intensive, however, requiring numerous steps with continual levels of loss of biological activity.

Purification of CM101 as presently known in the art provides an end material which is only 40% pure as measured by chemical analyses and biological assays. The other 60% comprises plant and yeast polysaccharides and endogenous bacterial polysaccharides. The plant and yeast contaminants originate for the most part in the additives to the commercial culture media used for optimal growth of the GBS bacteria. The endogenous contaminants include GBS polysaccharides including group and type specific antigens (Paoletti, L. C. et al., *Neonatal mouse protection against infection with multiple group B streptococcal* (*GBS*) *serotypes by maternal immunization with a tetravalent GBS polysaccharide-tetanus toxoid conjugate vaccine, Infect. Immun.* 62(8):3236–43 (1994); Michon, F., *Multiantennary group-specific polysaccharide of Group B Streptococcus, Biochem.*, 27:5341–51 (1988)). CM101 of this 40% purity level represents the current clinical grade. There is a need, therefore, for a purification method of CM101 which results in an end product with increased overall purity, preferably with the removal of extraneous plant and yeast polysaccharides and GBS antigenic polysaccharides.

Additionally, the purification scheme known in the art includes environmentally unsound steps, such as the use of a large volume of phenol in a phenol:water extraction. Phenol is a well-known caustic material.

Therefore, objects of the present invention are to provide a purification method resulting in (i) a material of high purity, (ii) using a minimal number of steps, (iii) minimizing the use of caustic or toxic materials such as phenol, and (iv) increasing the yield of material.

SUMMARY OF THE INVENTION

The above objects have been achieved with the invention described herein. Particularly, a purification scheme including a hydrophobic interaction chromatography (HIC) resin for purification of CM101 from GBS bacterial culture media results in a product of greater than 95% purity.

One aspect of this invention is a process for purifying a polysaccharide toxin from GBS bacteria, the process including the use of an HIC resin. The present invention also includes a substantially pure polysaccharide toxin from GBS bacteria produced by the method disclosed herein, and a pharmaceutical composition comprising a substantially pure toxin and a pharmaceutically acceptable carrier. The pharmaceutical composition may be used to treat a patient having a medical condition. For example, a tumor patient may be treated with the composition of the present invention.

BRIEF DESCRIPTION OF THE DRAWINGS

FIG. 5*a* is measured at UV 206 absorbance. FIG. 5*b* is measured at UV 280 absorbance.

DESCRIPTION OF SPECIFIC EMBODIMENTS

Figure 1:
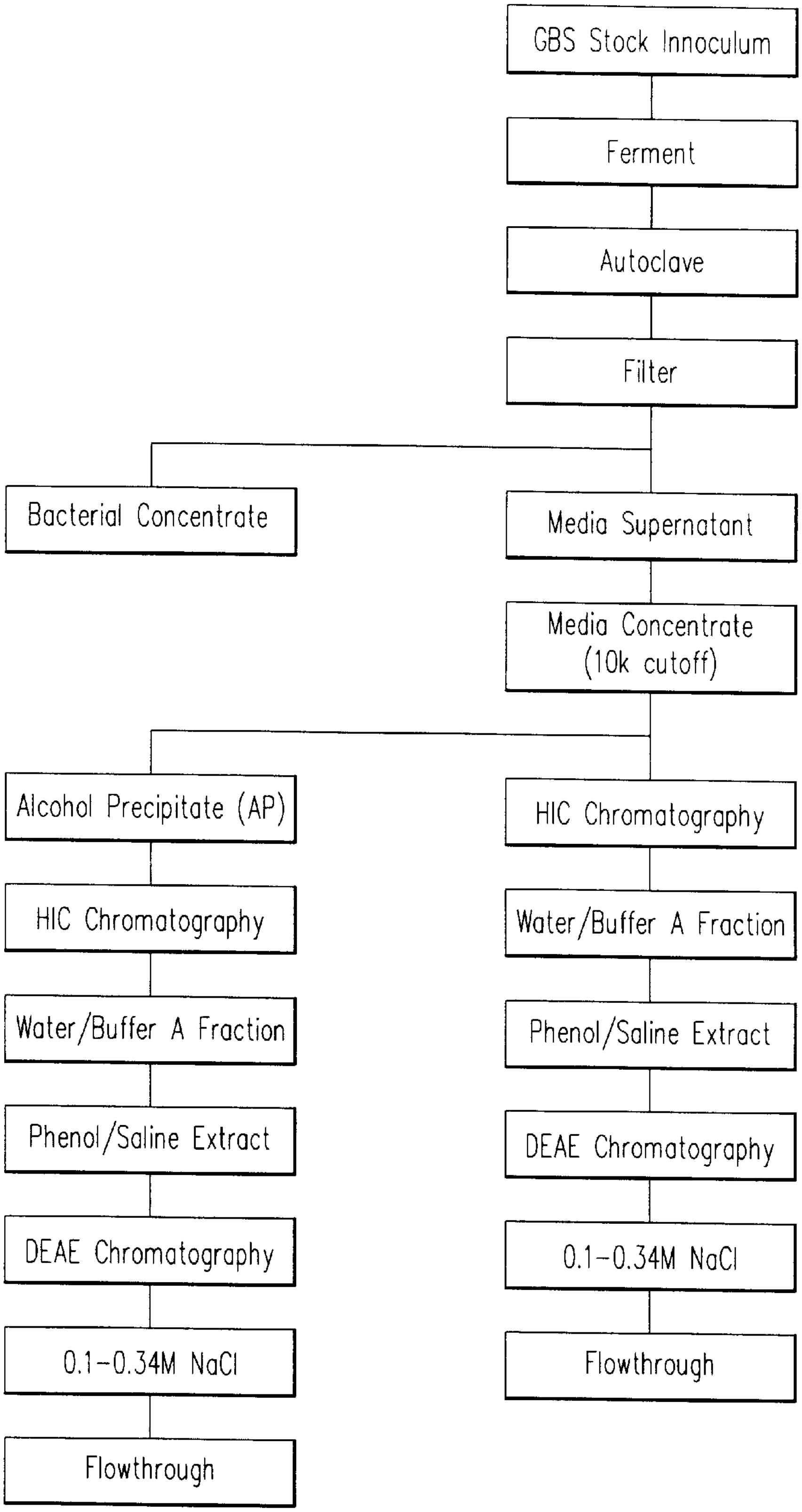
FIG. 1 illustrates a CM101 purification scheme of the present invention.

GBS toxin as used herein is defined as any fraction or component isolated from natural or lysed GBS bacteria, or derived from media supernatants of lysed and/or autoclaved GBS bacteria, and which has a biological activity of evidenced by induction of respiratory distress in the sheep assay (Hellerqvist, C. G. et al., *Studies on group B β-hemolytic streptococcus I. Isolation and partial characterization of an extra-cellular toxin., Pediatr. Res.,* 12:892–898 (1981)) or activation of complement and binding to neovasculature as demonstrated by a peroxidase-antiperoxidase (PAP) assay of a tumor tissue specimen (Hellerqvist, C. G. et al., *Anti-tumor effects of GBS toxin: a polysaccharide exotoxin from group B β-hemolytic streptococcus, J. Canc Res. Clin. Oncol.,* 120:63–70 (1993); and Hellerqvist, C. G. et al., *Early Results of a Phase I Trial of CM*101 *in Cancer Patients., Proceedings of the American Association of Cancer Research Annual Meeting* (1995)).

Substantially pure GBS toxin means a preparation in which GBS toxin is greater than 40% pure (e.g., present in a concentration of at least about 40% by weight), preferably at least approximately 60% pure, more preferably at least approximately 90% pure, and most preferably at least approximately 95% pure.

A source for GBS starting material for use in the method of the present invention may be obtained by culturing strains of Group B β-hemolytic Streptococcus bacteria that have recently infected or are capable of infecting newborn infants. Isolates of such strains may be obtained from the blood of infected infants.

High production of CM101 generally requires fermentation with the complex media THB which contains high molecular weight material in the form of polysaccharides and proteins for GBS optimum growth and CM101 production. During the fermentation process, the bacteria produce from the nutrients quantities of proteins, nucleic acids, and polysaccharides other than CM101. The estimated concentration of CM101 in the fermentation broth is less than 0.1% by weight.

The purification method of the present invention employs hydrophobic interaction chromatography (HIC) which eliminates the bulk of the endogenous and exogenous contaminating proteins, nucleic acids, and polysaccharides more efficiently than known methods and results in an end product which contains 10–50% pure CM101. In just one step of contacting the GBS starting material and the HIC resin, this represents a 100–500 fold purification from the starting material.

Use of an HIC resin for purification of a polysaccharide is surprising and novel because HIC columns are designed for purification of hydrophobic proteins and are not believed useful for polysaccharides free of proteins and lipids. Polysaccharides are generally characterized as being hydrophilic due to their numerous hydroxyl groups. Application of a starting material to an HIC column under the conditions recommended by the manufacturer and used by practitioners skilled in the art would therefore be with the intention of retaining proteins and allowing polysaccharides to pass through the column unbound.

The surprising discovery is that CM101 has hydrophobic properties that allow use of the present purification scheme to achieve a high level of purity. Especially surprising is that CM101 has significantly more hydrophobic characteristics than most of the proteins and polysaccharides present in the supernatant from which the CM101 is isolated. Greater than 98% of these protein and polysaccharide contaminants pass through the HIC column.

Although the HIC resin is generally employed in an HIC column, this step alternatively may be performed by contacting the resin and the starting material in some other manner. For example, the GBS source and the resin may be placed in a vessel together in a batchwise process, and the toxin-containing portion subsequently separated from the resin as by centrifugation.

Additional purification steps may include a phenol/saline extraction in a small volume relative to the prior methods (approximately 1000-fold reduced) and an ion exchange column. These additional purification steps contribute to an end product with greater than 95% purity.

HIC is a method used to separate proteins, such as membrane proteins, based on their hydrophobic nature. An HIC resin is defined as a resin having interactive hydrophobic groups which are generally covalently attached to a support such that the hydrophobic groups are free to interact with substances in contact with the resin. Examples of hydrophobic groups include alkyl, alkoxy, and aryl groups. The preferred HIC resin to be used in accordance with the present invention has a support with attached aliphatic groups of two or more carbons, preferably alkyl groups in the range of 2 to 12 carbons, and more preferably normal or branched butyl groups. Phenyl groups or alkoxy groups of up to 20 carbons are also preferred interactive hydrophobic groups. The interactive hydrophobic groups are preferably supported by Sepharose (Pharmacia) or acrylamide (Toso Haas, Montgomeryville, Pa.). According to the standard procedure for use of an HIC column, the starting material containing the protein of interest is applied to the column in up to 2 M aqueous salt solution and the bound proteins are then eluted and separated through decreases in hydrophobic interactions by reducing the ionic strength of the developing buffer. Changes in pH and/or temperature may also be used to alter the hydrophobic interactions.

CM101 purification from Group B Streptococcus requires obtaining a bacterial culture of GBS. Bacterial innocula are incubated to late log phase in Todd Hewitt Broth (THB) modified by supplementation with 2 g/l or more of glucose and $Na_2HPO_4$. As indicated in FIG. 1, the culture is then autoclaved. CM101 is present in the supernatant of GBS fermentation cultures at a concentration of 2–15 mg/l following autoclaving. The media contains approximately 15 g/l of other bacterial and media components. Thus, CM101 constitutes approximately 0.01–0.1% of the components in the supernatant. After autoclaving, the media is filtered. The filtrate is concentrated via a 10,000 Dalton (10k) cutoff filter.

CM101 is then purified in accordance with this invention, as shown in FIG. 1, by applying a supernatant concentrate or reconstituted alcohol precipitate thereof made 2 M in potassium phosphate or another salt, such as sodium phosphate, sodium or potassium sulphate, chloride, or acetate, to an HIC column preferably equilibrated in the same salt of the same molarity. The method wherein the media concentrate, or 10k, starting material is employed without alcohol precipitation and reconstitution is preferred because the media concentrate starting material provides higher yield of CM101 than does the reconstituted alcohol precipitate.

The CM101-containing starting material is applied to the HIC column and washed with aqueous 2 M phosphate. Following a 2 M wash, the column is further developed with 1 M and 0.25 M salt, preferably phosphate. In the preferred embodiment, the CM101 is eluted from the column with water as a single peak containing 10–50% CM101. Alternatively, water is replaced for CM101 elution from the HIC column with 10 mM phosphate, pH 6.8 in 10% ethanol in water (Buffer A), followed by 20% ethanol in water. CM101 activity is recovered in both the Buffer A and 20% ethanol fractions. Use of Buffer A is generally not sufficient to remove all the CM101 from the HIC column, so the Buffer A wash is followed by an additional 20% ethanol wash. However, in scale-up, the ethanol constitutes an environmental hazard and the subsequent phenol/saline extraction of the water peak or the Buffer A and 20% ethanol peak fractions yields CM101 of approximately equal purity. The HIC procedure removes better than 98% of both the proteins and media polysaccharides remaining in the 10k concentrate or the reconstituted alcohol precipitate.

The enriched CM101 from the HIC column may be further purified by an extraction in phenol and an aqueous salt solution, preferably 0.05 M saline. This additional step provides a CM101 fraction of approximately 95% purity.

The water or the combined Buffer A and 20% ethanol fractions eluted from the HIC column are either dialyzed against water and lyophilized and reconstituted in 0.05M saline or dialyzed against saline after concentration. Typically, phenol is added to the material and the solution is rapidly heated to 70–80° C. When a single phase forms, the solution is chilled to 4° C. The resulting saline phase of the phenol/saline extraction contains CM101 and may then be applied to a cation exchange column, such as DEAE.

For the DEAE column procedure, the DEAE column is equilibrated in water and then washed with 0.1 M saline, 0.05 M NaOAc, pH 7.4 and developed with a step gradient to 0.34 M NaCl. Elution of CM101 is monitored and quantitated with an ANA-1 assay. As with the HIC resin step, an ion exchange resin may be contacted with the toxin-containing material through use of equipment other than a column. The CM101-containing fraction is then dialyzed against water and lyophilized. After the phenol/saline extraction and ion exchange steps, CM101 is greater than 95% pure.

The column eluates, or material resulting from the resin contact steps, are assayed for biologic activity with the ANA-1 assay. The biological activity is then confirmed with a sheep assay. Table 1 depicts several separations of AP and 10k material obtained from different batches of starting materials and applied to the HIC column. Removal of denatured protein and media polysaccharides and other material is similar.

Although the preferred order of purification is to perform the HIC step, followed by the phenol/saline extraction, and then the ion exchange step, purification may also be performed in another order.

Figure 2:
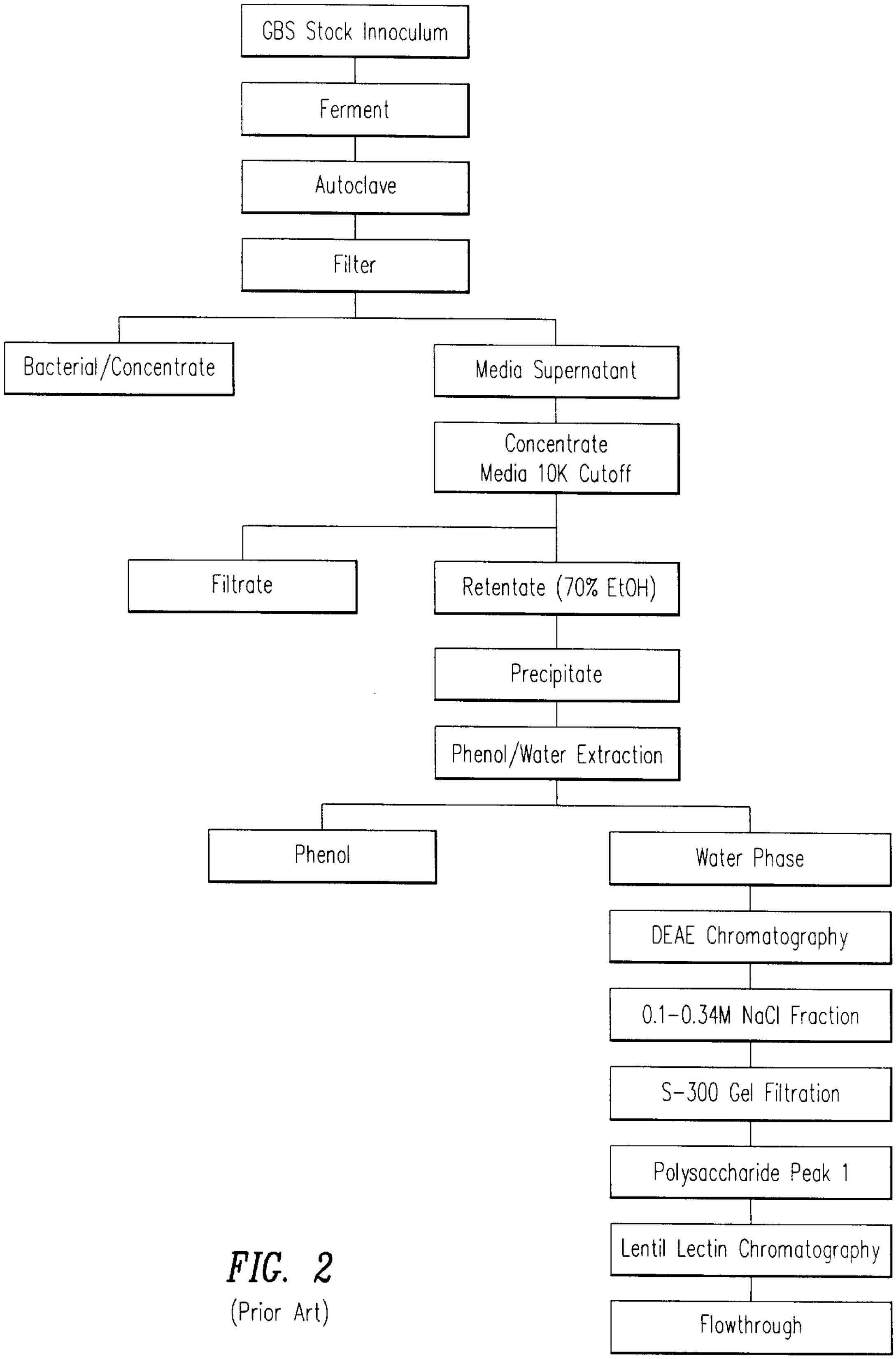
FIG. 2 illustrates a known CM101 purification scheme.
Figure 3A:
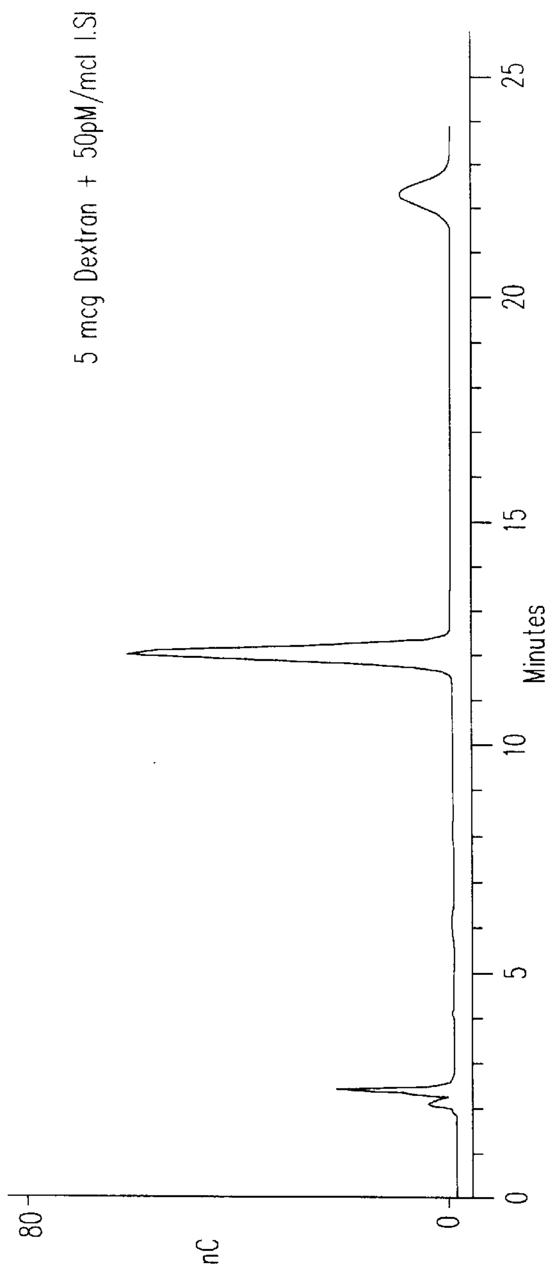
FIGS. 3*a*–3*a* are quantitative hydrolysis standard curves showing the dose response of a PAD detector for 5 μg (FIG. 3*a*), 20 μg (FIG. 3*b*), and 50 μg (FIG. 3*c*) of dextran (a glucose polymer) with 6-deoxy glucose as a constant internal standard.
Figure 3B:
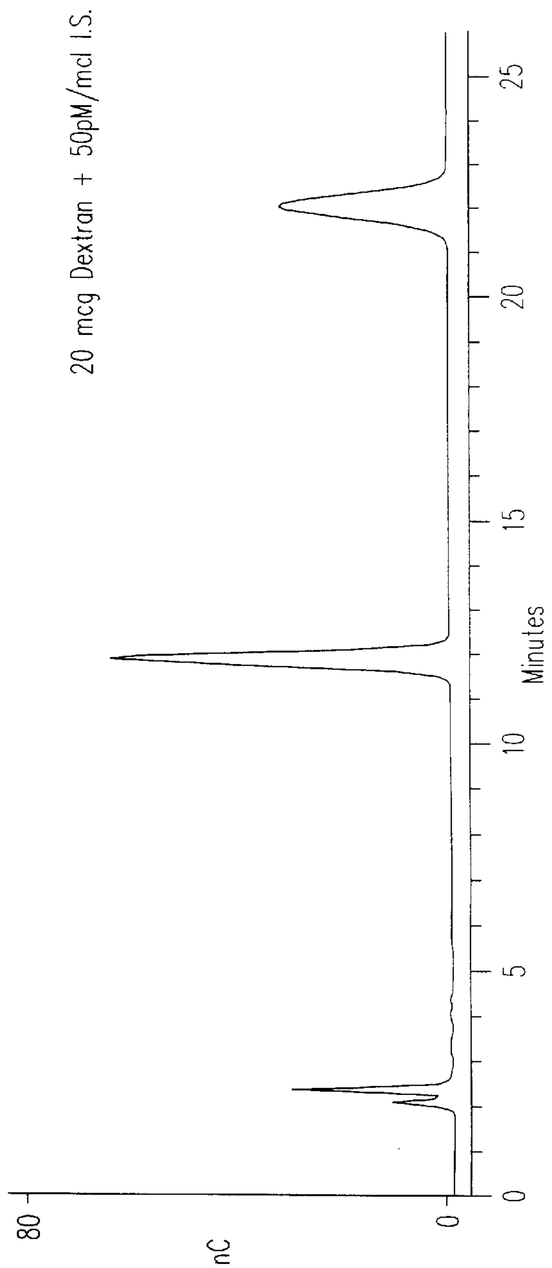
Figure 3C:
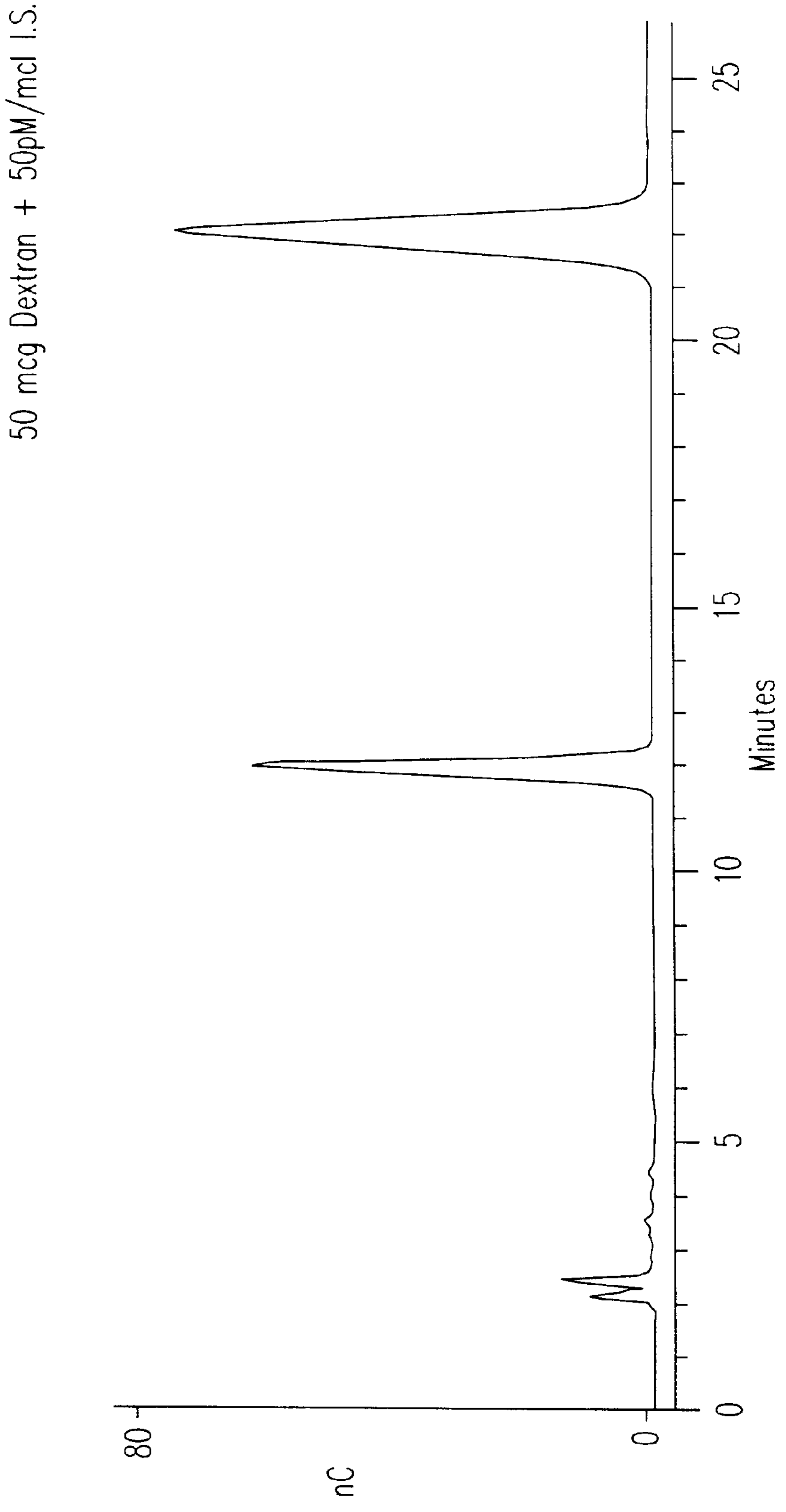

FIG. 2 presents an example of a known method of CM101 purification. Notably, a 70% ethanol precipitate step is used, followed soon thereafter with a phenol/water extraction. The large volumes of ethanol and phenol required at these early stages of the known purification method represent environmentally unsound practices. The method represented in FIG. 2 also requires an ion exchange column, a gel filtration column, and a lentil lectin column.

The prior method contains numerous steps, including environmentally hazardous ones. On the other hand, the method of the present invention is effective, gives higher purity and 2 to 25 times the yield, and minimizes use of environmentally unsound materials.

The environmentally hazardous phenol-water extraction step is reduced 1000-fold as compared to the previously used procedures. Furthermore, additional purification as by a gel filtration procedure is eliminated. The lentil lectin chromatography step of the prior method is also deleted. The end product of the HIC column, phenol/saline extraction, and ion exchange column steps has approximately 95% purity, so other treatments are unnecessary.

The CM101 purified by the method of the present invention may be used for research or therapeutic purposes. The CM101 is particularly useful when combined with a pharmaceutically acceptable carrier, e.g., reconstituted in saline and administered to a patient intravenously. Other dosage forms to administer purified CM101 may also be used. The pharmaceutical composition of this invention comprises the substantially pure GBS toxin of this invention in combination with a pharmaceutically acceptable carrier. In general, the carrier will be one that is readily mixed with the toxin to form a composition that is administrable by intravenous (IV) means. Thus, the carrier is preferably water, which may have other pharmaceutically acceptable excipients included to ensure its suitability for intravenous administration. The resulting composition will be sterile and will have acceptable osmostic properties. In general, a suitable IV formulation is prepared in accordance with standard techniques known to one of skill in the art. For example, Chapter 85 entitled "Intravenous Admixtures" by Salvatore J. Turco in the Eighteenth Edition of Remington's Pharmaceutical Sciences, Mach Publishing Co. (1990), incorporated herein by reference, provides standard techniques for preparing a pharmaceutically acceptable IV composition useful in accordance with this invention.

Additionally, a patient having a medical condition which is found to respond advantageously to CM101 may be treated with a pharmaceutical composition of the present invention. For example, a patient having a tumor may be advantageously treated by intravenously administering the pharmaceutical composition taught herein. U.S. Pat. No. 5,010,062 discusses the treatment of certain tumors in humans and is incorporated herein by reference.

Quantitative and Qualitative Analysis

HPLC Analysis

The purity and amount of CM101 obtained from a sample after HIC chromatography is established by high pressure liquid chromatograph (HPLC) gel filtration analysis. The gel filtration column is typically equilibrated with an ammonium acetate ($NH_4OAc$) buffer, pH 8.4, and the biologically active CM101 is eluted as an included homogeneous narrow peak.

A typical detector response (UV 203 absorption) using 30, 50, and 100 $\mu$g pure CM101 standards injected in 100 $\mu$l of developing buffer on a Hydragel 1000 column (Waters, Millford, Mass.) is $26\times10^6$, $48\times10^6$, and $97\times10^6$ area units, respectively which yields a dose response curve for quantitation of unknown samples.

Amino Acid Analysis

Quantitative and qualitative automated amino acid analysis may be performed with standard commercially available equipment, e.g., PicoTag, available from Waters, Millford, Mass.

ANA-1 Assay

To monitor the biological activity of the different fermentation and purification steps, an in vitro assay employing a transformed mouse macrophage cell line may be used. The assay measures IL-6 production of the mouse macrophage ANA-1 in response to CM101 exposure.

Particularly, CM101 induces raf/myc transformed murine bone marrow macrophage cell line ANA-1 to respond in vitro by IL-6 production. Other macrophage-like cell lines and fresh peripheral blood leukocytes can also be used.

To perform the ANA-1 assay, samples are first diluted to the appropriate range (depending on the expected level of CM101 activity) and four to eight concentrations are tested at 1:4 dilutions. A CM101 standard curve using clinical grade CM101 reconstituted in PBS is generated. A 4000 ng/ml solution, which gave a 2000 ng/ml final concentration after the cells were added, was made in PBS, along with six serial 1:2 dilutions. Cells at a concentration of $2\times10^6$/ml may be used, for example. Sensitivity of the assay was increased by adding 200 U/ml murine IFN-γ to the ANA-1 cells. Final cultures were 100 U/ml IFN-γ.

The microtiter plate with cultures should be placed in a 37°, 5% $CO_2$-in-air, humidified incubator overnight (16–18 hours), and then be followed by an ELISA IL-6 Assay (R. D. Systems, Minneapolis, Minn.). Specifically, culture supernatants are transferred to the IL-6 assay plate and the plate is held at 4° C. until the IL-6 assay is complete.

Sheep Pulmonary Arterial Pressure Assay

The toxin affects sheep lungs by increasing pulmonary hypertension, manifested by increased pulmonary arterial pressure and by increased lung vascular permeability.

CM101 samples in phosphate buffered saline (PBS) may be administered to lambs by infusion and changes in pulmonary arterial pressure recorded at 15 minute intervals. These changes in pressure are correlated to CM101 activity. (Hellerqvist, C. G. et al., *Studies on group B β-hemolytic streptococcus I. Isolation and partial characterization of an extra-cellular toxin., Pediatr. Res.,* 15:892–898 (1981)).

Sugar Analysis

A 100 μg quantity of a sample is hydrolyzed for two hours at 100° C. in a mixture of trifluoroacetic acid (TFA), acetic acid (HOAc) and water in a ratio of 5:70:25. The solution is evaporated and the sample is further hydrolyzed for two hours at 100° C. in a mixture of TFA and water in a ratio of 2:8. This process completely hydrolyzes all glycosidic linkages in the sample. The N-acetyl groups originally present on the amino sugars are also removed.

Figure 4:
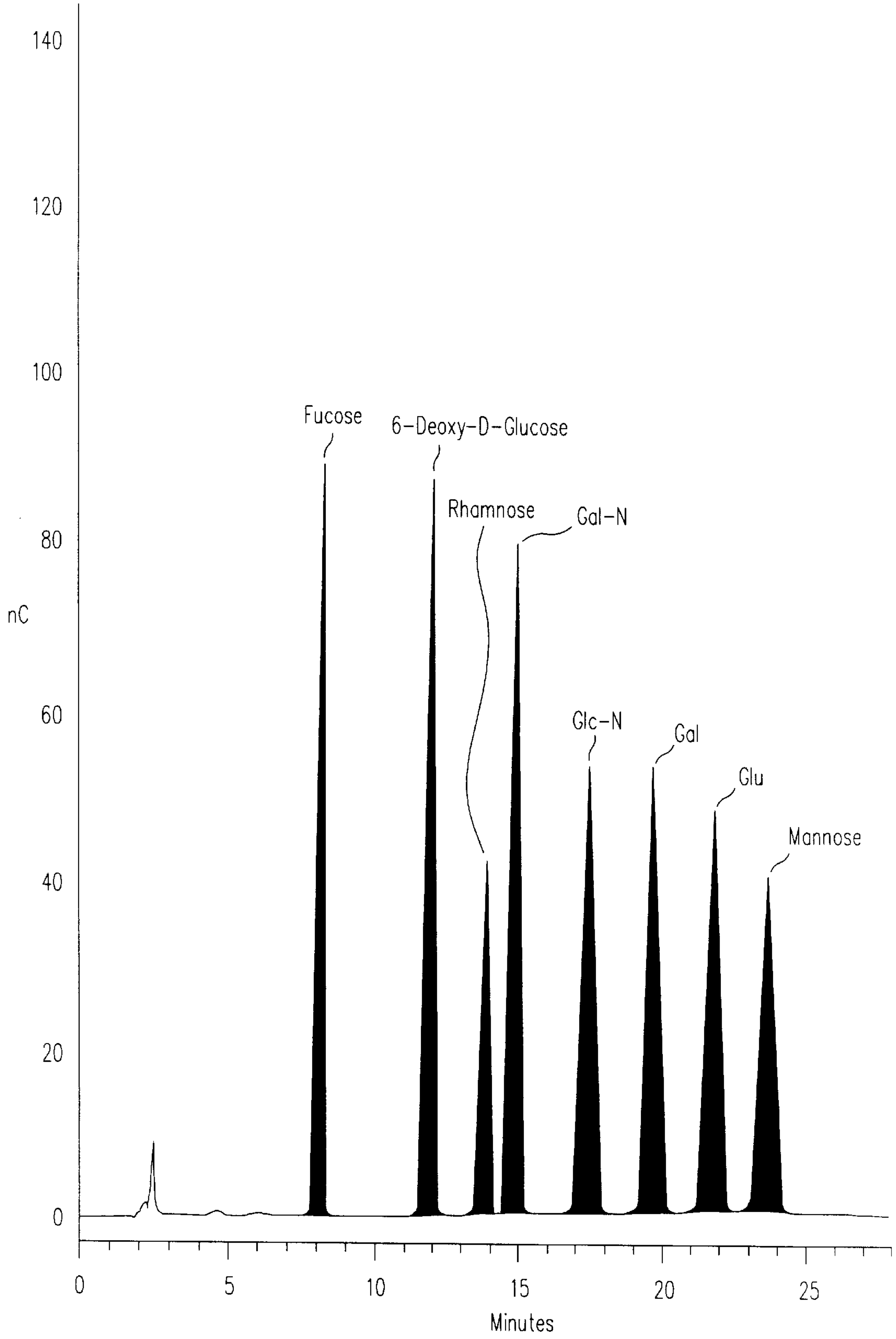
FIG. 4 shows the separation of standard sugar samples.

The samples are then analyzed on the Dionex sugar analysis system using a PAD (Pulsed Amperometric Detection) detector. The resolution is illustrated in FIG. 4.

The purity of the sample is established by quantitative and qualitative sugar analysis. The principle is illustrated in FIGS. 3*a*–3*c* and FIG. 4. A sample of polysaccharide quantitated by HPLC is supplemented with an internal standard 6-deoxy-D-glucose hydrolyzed and analyzed. The method described in this section gives a linear dose response in the range tested and qualitative analysis is accomplished by comparing retention times of unknowns with the standards.

EXAMPLES

Example 1

A scaled-up purification scheme for CM101

A Group B Streptococcus isolate Type III working stock was used in conjunction with a 3,000 gallon fermentor. A 25 ml seed of the bacterial culture is used for an 80 liter vessel with a 65 liter working volume (lwv) which is then used to inoculate a 750 lwv vessel, and which, in turn, goes into the final 7500 lwv (3,000 gallon) fermentor. Alternatively, the 65 lwv may be used to innoculate the 7500 lwv fermentor directly.

The cultures are terminated at late log phase by autoclaving. The bacteria are then removed by continuous centrifugation at 10,000×g, followed by 0.45 micron cassette filtration (Millipore Corporation, Bedford, Mass.).

The resulting culture supernatant is then concentrated 15-fold through cassette filtration using 10 kD cut off cassettes (Millipore) to 500 liters. The concentrated material is then made 2 M in salt, preferably sodium phosphate, pH 7.4 (loading buffer) by dialysis.

The concentrated supernatant is then subjected to hydrophobic interaction chromatography, through the use of a 60 liter n-butyl Sepharose column (Pharmacia, Uppsala, Sweden) using a BioPilot system (Pharmacia). The capacity of the n-butyl Sepharose resin for the biologic CM101 activity in the media concentrate with no flow-through of activity is approximately 80 liter of media to one liter of resin. After the concentrated supernatant is loaded onto the column, the column is washed with the loading buffer followed by 1 M and 0.25 M phosphate buffer, pH 7.4. The CM101-containing fraction is eluted with water in approximately 120 liters or two column volumes and concentrated to 2 liters in a 10 kD cut-off cassette. The column elution is controlled by a preestablished program in the BioPilot and the eluate is monitored by UV absorption at 206 and 280 nm, conductivity, and pH.

The CM101-containing 2 liter fraction is dialyzed against 0.05 M saline, pH 7.0 and then heated to the range of 75–80° C. and 0.2–2 liters of phenol are added. The mixture is then heated to 80° C. and maintained at that temperature for 5 minutes. Following this, the mixture is chilled to 4° C. The water phase resulting from this step is applied to a DEAE Sephacel FF column (Pharmacia, Uppsala, Sweden) equilibrated in water. The column is washed with 100 mM saline, 0.05 M NaOAc, pH 7.4, and the biologically active material, CM101, is then eluted from the DEAE column with a NaCl gradient. The biological activity is detected by Il-6 assay and HPLC analysis. The quality of the CM101 purified through this procedure is established by HPLC and sugar analysis as well as biological activity assays by Il-6 and sheep tests.

This scaled up purification scheme provides the advantage of avoiding the large volume, early phenol-water extraction procedure of the alcohol precipitate used in the previous procedure.

Results

Figure 5A:
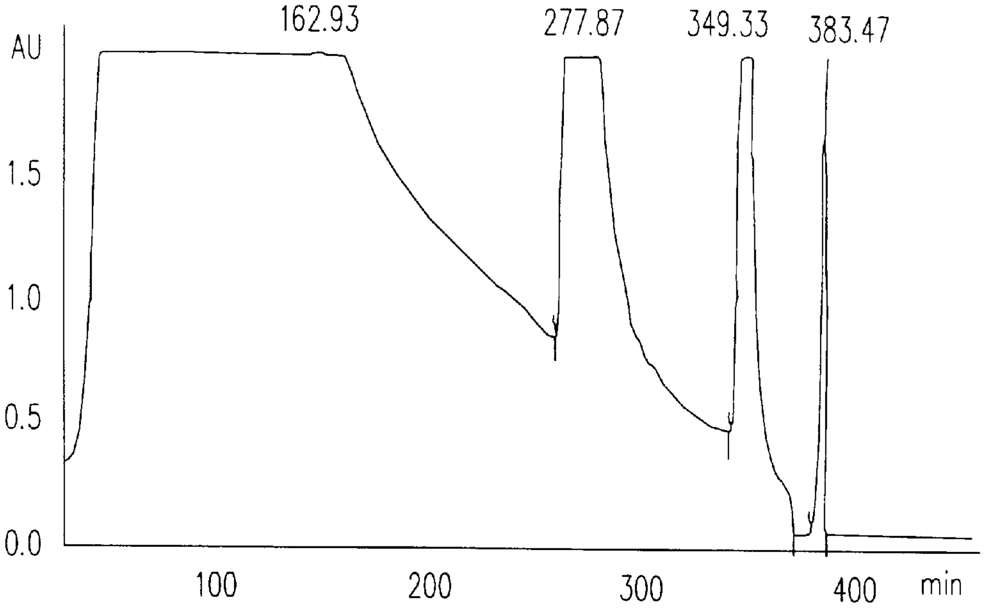
FIGS. 5*a*–*b* are elution profiles of a media concentrate on a butyl-Sepharose HIC column.
Figure 5B:
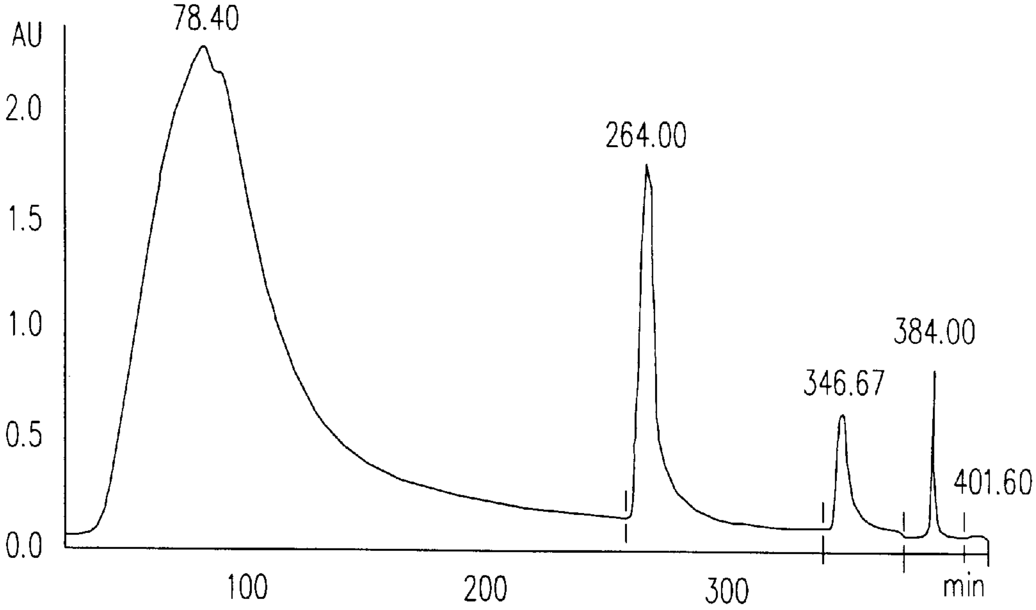

FIGS. 5*a–b* show elution profiles of a media concentrate on a butyl-Sepharose HIC column in 2 M $K_2HPO_4$, pH 7.2. The various peaks are the results of timed step-wise changes in the elution gradient. FIG. 5*a* represents the profile measured at UV 206 absorbance, which quantitates the peak fractions for total organic material, and shows the CM101 in the last narrow peak (approximately 383 minutes). FIG. 5*b* represents the profile measured at UV 280 absorbance, which quantitates the amount of protein in the different fractions.

By performing the HIC column step, CM101 is caused to bind to the column whereas up to 99.7% of the protein and up to 98.5% of neutral and charged polysaccharides pass through the column, as indicated in Table 1.

TABLE 1

Purification of CM101 Activity by HIC Chromatography
Quantitation by Integration of UV 280 and 206 Profiles

| | | Final Elution Possible Protein UV280 Recovered % | Total Organic UV206 Recovered % |
|---|---|---|---|
| AP 6P6 | Water | 0.85 | 2.67 |
| AP 2P9 | Water | 1.08 | 0.19 |
| 10K5P6 | Water | 0.82 | 1.05 |
| 10K5P6 | Water | 0.46 | 2.43 |
| AP 1 P9 | Buffer A | 0.39 | 1.90 |
| 10K5P6 | Buffer A | 0.50 | 1.51 |
| AP 6P6 | Buffer A | 0.19 | 1.35 |

In Table 1, different fermentation lots as alcohol precipitates (AP), AP1, AP2, and AP6, and 10k concentrates were subjected to HIC chromatography and eluted with either water or Buffer A. Both processes yield approximately the same efficacious removal of exogenous and endogenous protein (UV 280) and polysaccharides and general organics (UV 206).

Figure 6A:
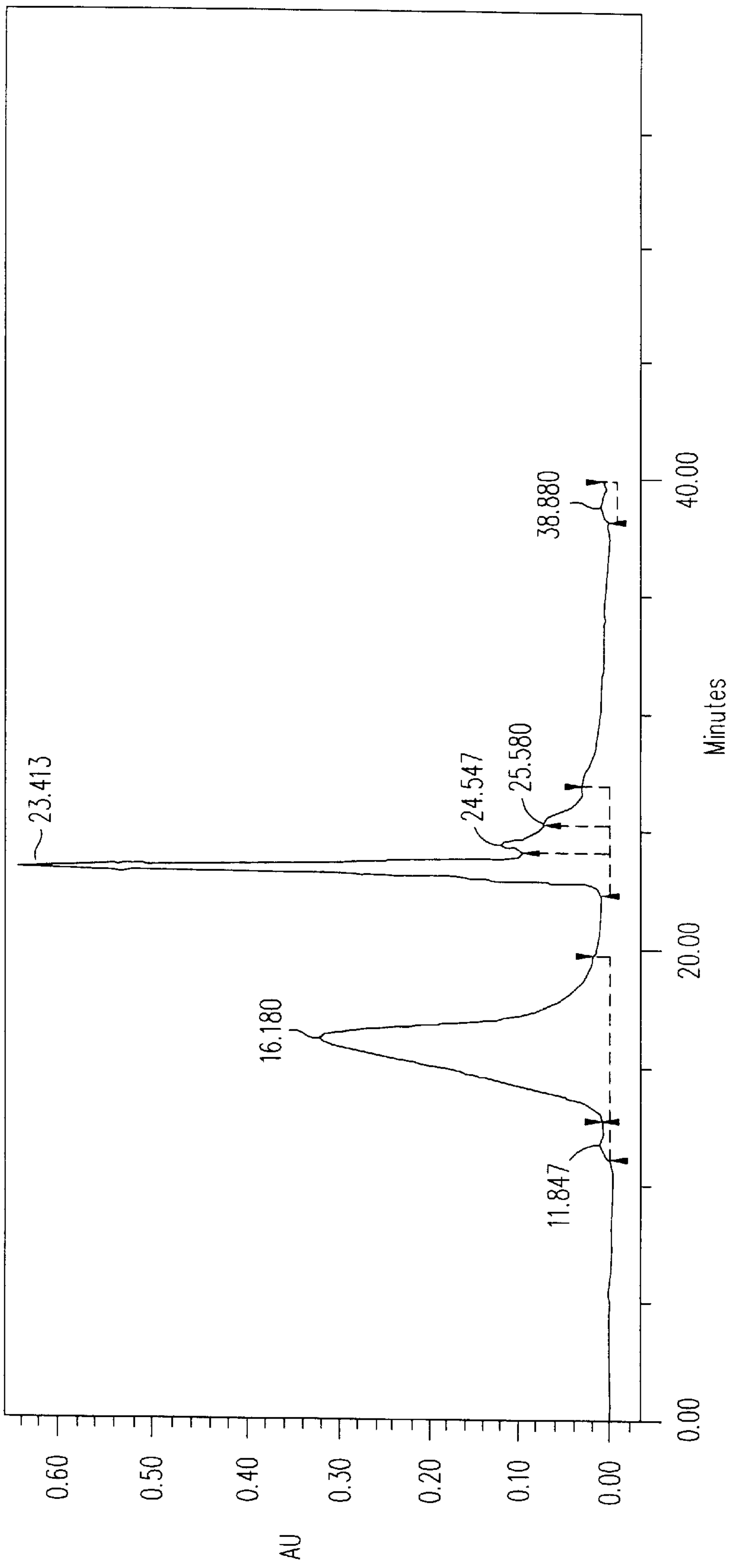
FIG. 6*a* is an HPLC profile of an HIC-purified water-eluted fraction containing CM101 (16 min peak) and monitored at UV 203 absorbance on a Millenium 2000 Diodo-Ray detector (Waters, Millford, Mass.).
Figure 6B:
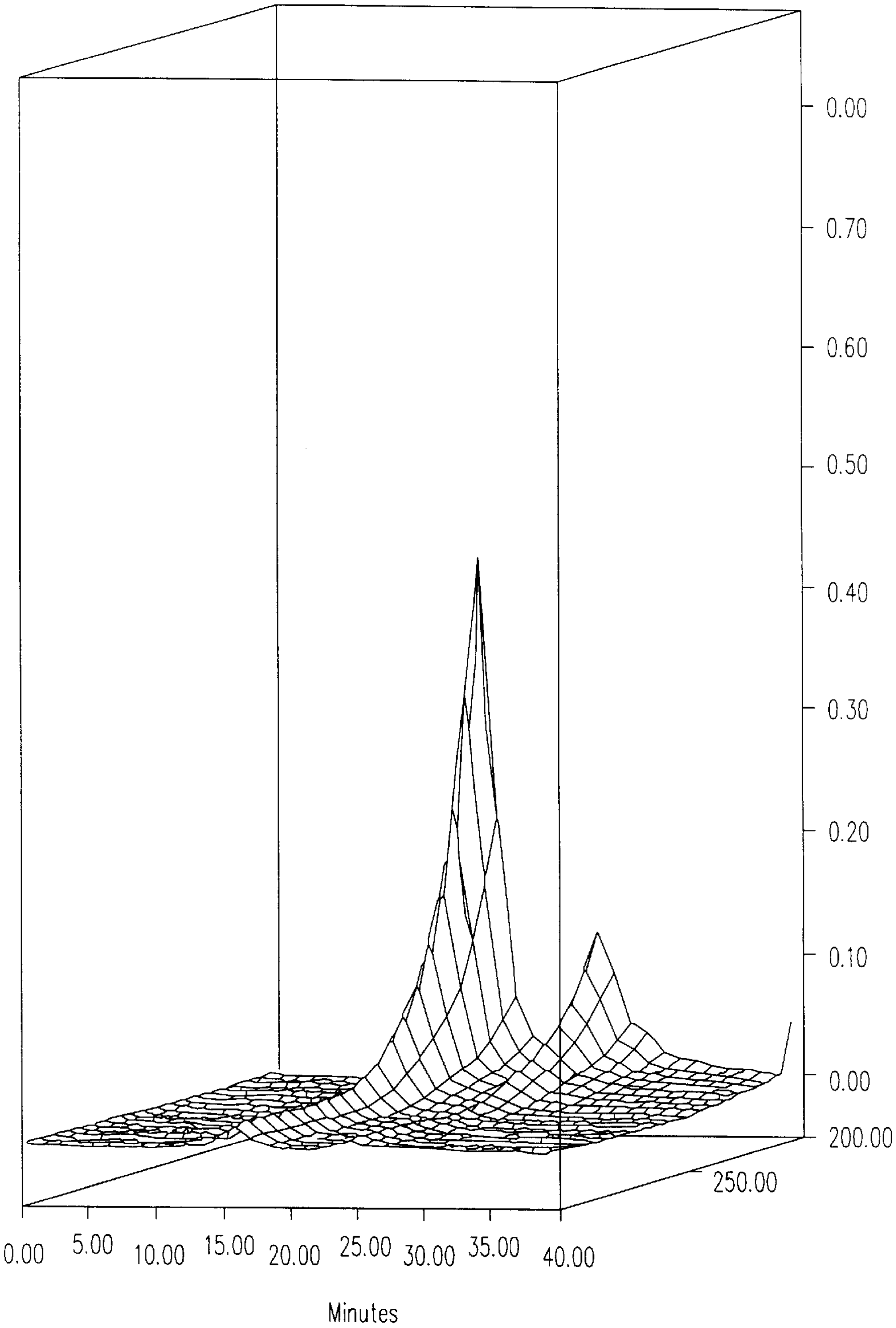
FIG. 6*b* is a Diodo-Ray spectrum corresponding to FIG. 6*a* and illustrating minimal presence of 260 absorption (RNA and DNA) and 280 absorption (tyrosine-containing protein) for the CM101 containing (16 min) peak.

FIGS. 6*a–b* present an HPLC profile, and a Diodo-Ray spectrum, of an HIC-purified water-eluted fraction containing CM101 and monitored at UV 203 absorbance. These figures illustrate the minimal presence of 260 absorption (RNA and DNA) and 280 absorption (protein) for the CM101 containing peak.

Figure 7A:
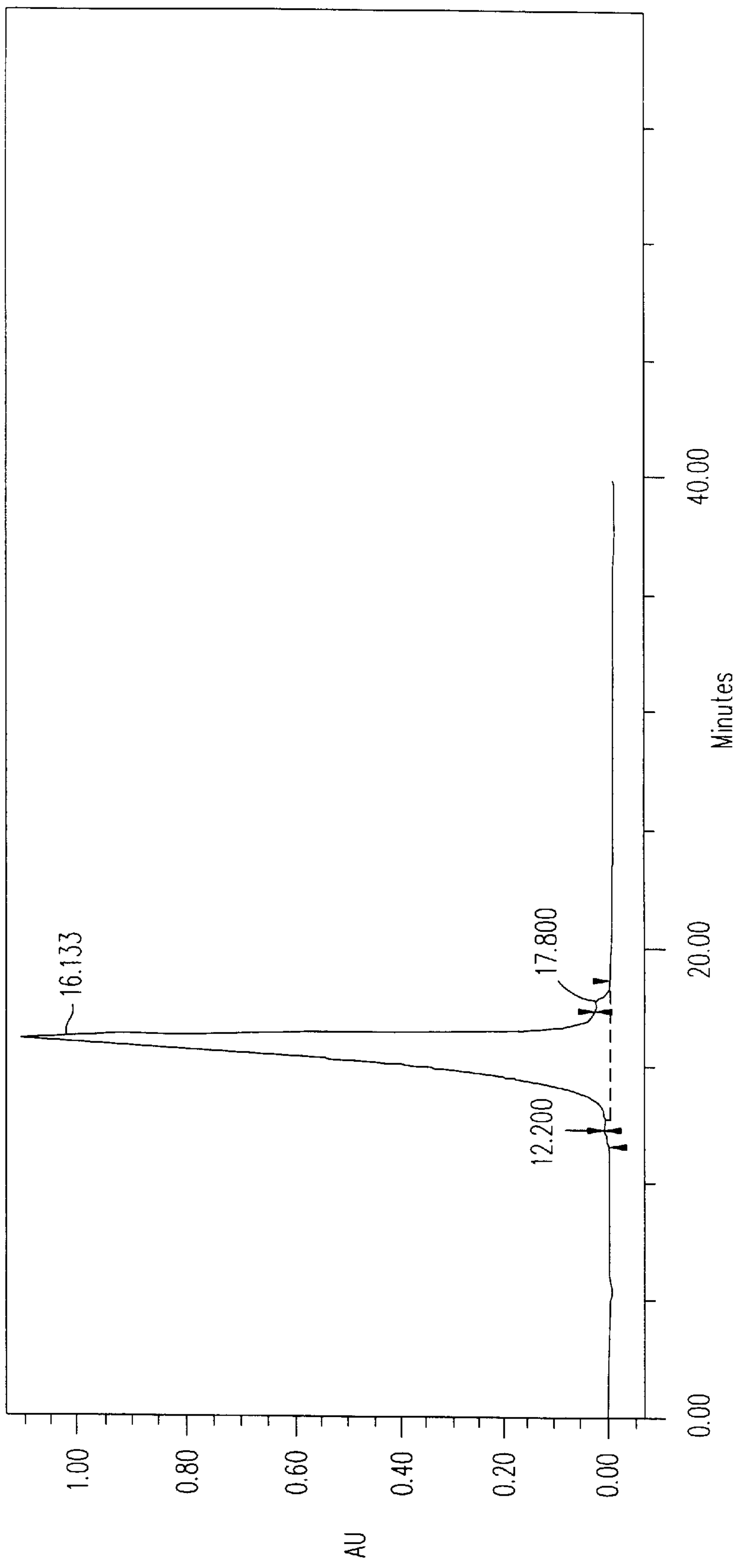
FIG. 7*a* is an elution profile monitored at 203 nm showing the purity of the HIC water-eluted peak of FIG. 6*a* further subjected to phenol/saline extraction and subsequent DEAE chromatography.
Figure 7B:
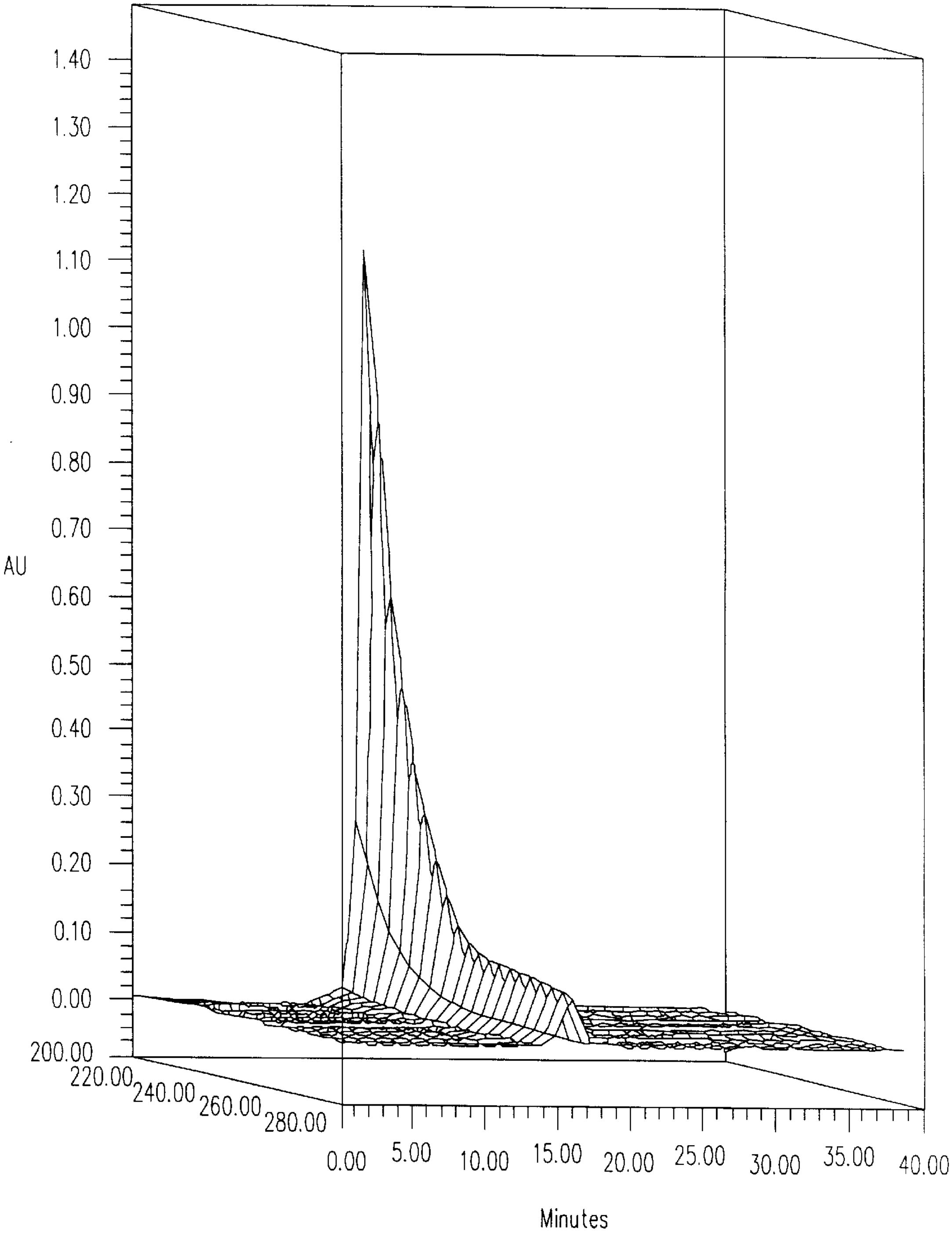
FIG. 7*b* is a Diodo-Ray spectrum illustrating the purity of the CM101-containing peak of FIG. 7*a* as evidenced by the narrow symmetric peak and the lack of absorption at 260 nm (RNA/DNA) and 280 nm (protein).

After the HIC fraction is further subjected to the phenol/saline extraction and ion exchange steps, the purity of the HIC water-eluted peak is further improved, as seen in FIGS. 7*a–b*. Note the narrow symmetric peak and the lack of absorption at 260 (RNA/DNA) and 280 (protein).

These elution profiles as well as the biological activity are similar to those obtained when the alcohol precipitate is used as the starting material for the HIC column.

Figure 8:
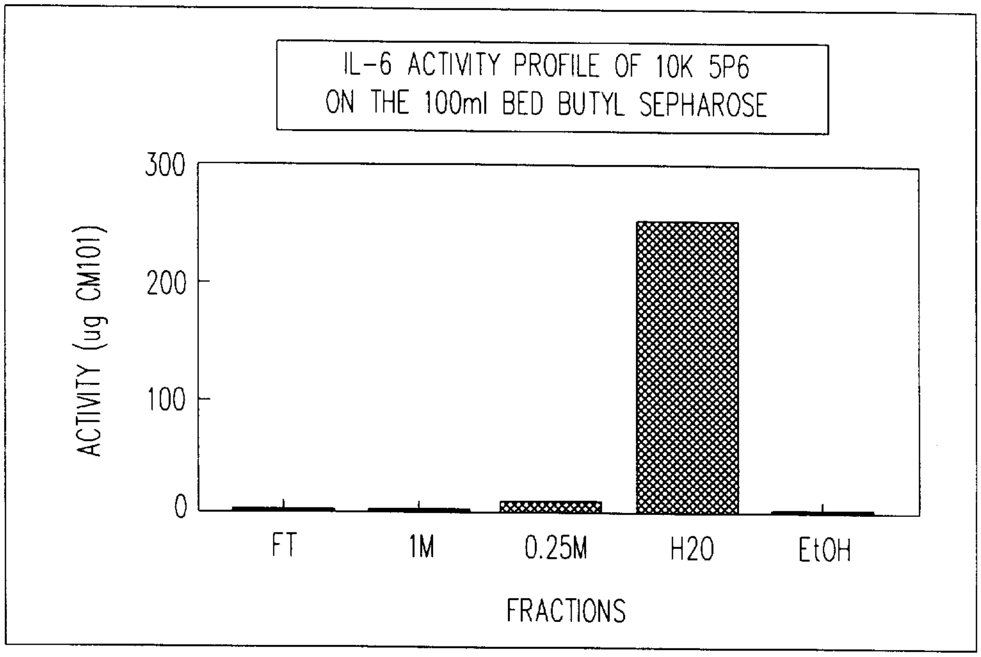
FIG. 8 is a profile of IL-6 activity by ANA-1 Assay of fractions from obtained from an HIC column.

The ability of the HIC fractions from the 10k starting material to induce IL-6 synthesis in ANA-1 cells is illustrated in FIG. 8. HIC chromatography yielded an approximate recovery of 50% of the total biologic activity in the media supernatant as measured by an ANA-1 Assay.

The different fractions obtained from the 10k concentrate after HIC chromatography were also tested in the sheep model for biologic activity. The amount of CM101 activity is determined based on a dose response curve using current clinical CM101 (1 Unit of activity corresponds to 7.5 $\mu$g/kg). The results are shown in Table 2 wherein HIC fractionations of alcohol precipitate (AP) and media concentrate (10k) are compared.

TABLE 2

Biologic Activity in Sheep of Fractions Obtained from HIC Chromatography of AP and 10K Material

| Fraction | Alcohol Precipitate (AP) CM 101 Activity $\mu$g/l | Media Concentrate (10k) CM 101 Activity $\mu$g/l |
|---|---|---|
| Pre-Load | 466 | Not Available |
| 1M Phosphate | 118 | 209 |
| 0.25 Phosphate | 28 | 2970 |
| Water | 225 | 7520 |

The product yield of the method of the present invention is also evidenced above, as the known methods provide about 300 $\mu$g of CM101 per liter of fermentation volume, as compared with the 7520 $\mu$g/l value shown above.

Figure 9:
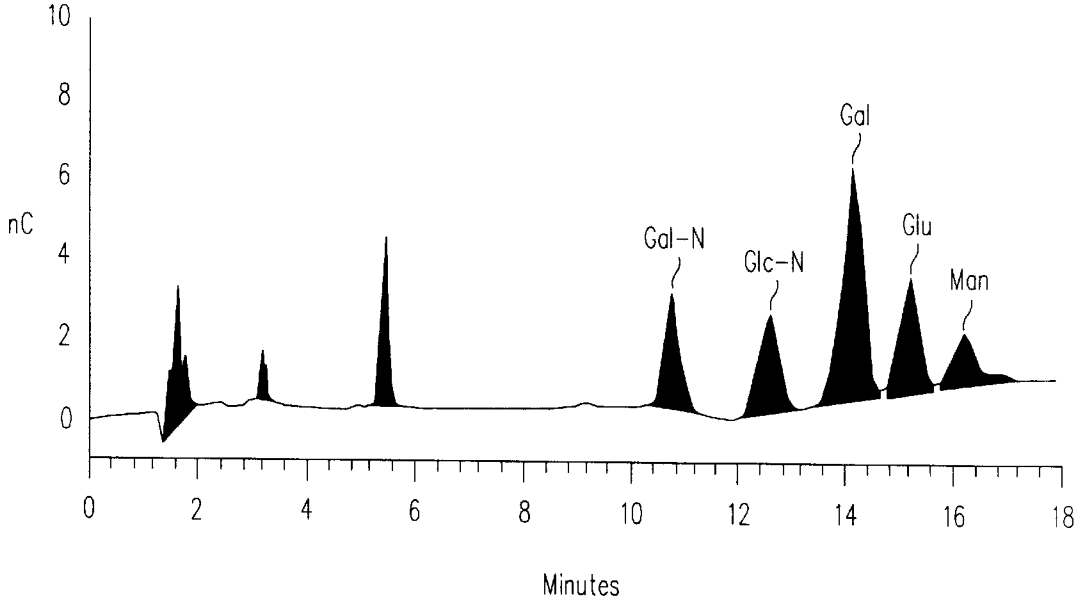
FIG. 9 illustrates a sugar analysis of CM101 purified by the method of the present invention.

The purified CM101 illustrated in FIGS. 7*a–b* obtained by the process of the present invention was also subjected to sugar analysis. The sugar yields are shown in FIG. 9.

Quantitatively, the CM101 obtained by the method of the present invention is greater than 95% pure carbohydrate and contains less than 5% of protein established by quantitative and qualitative as presented above and by automated amino acid analysis (PicoTag, Waters, Millford, Mass.).

Example 2

Comparison of Current Clinical Grade and New Composition

Figure 10:
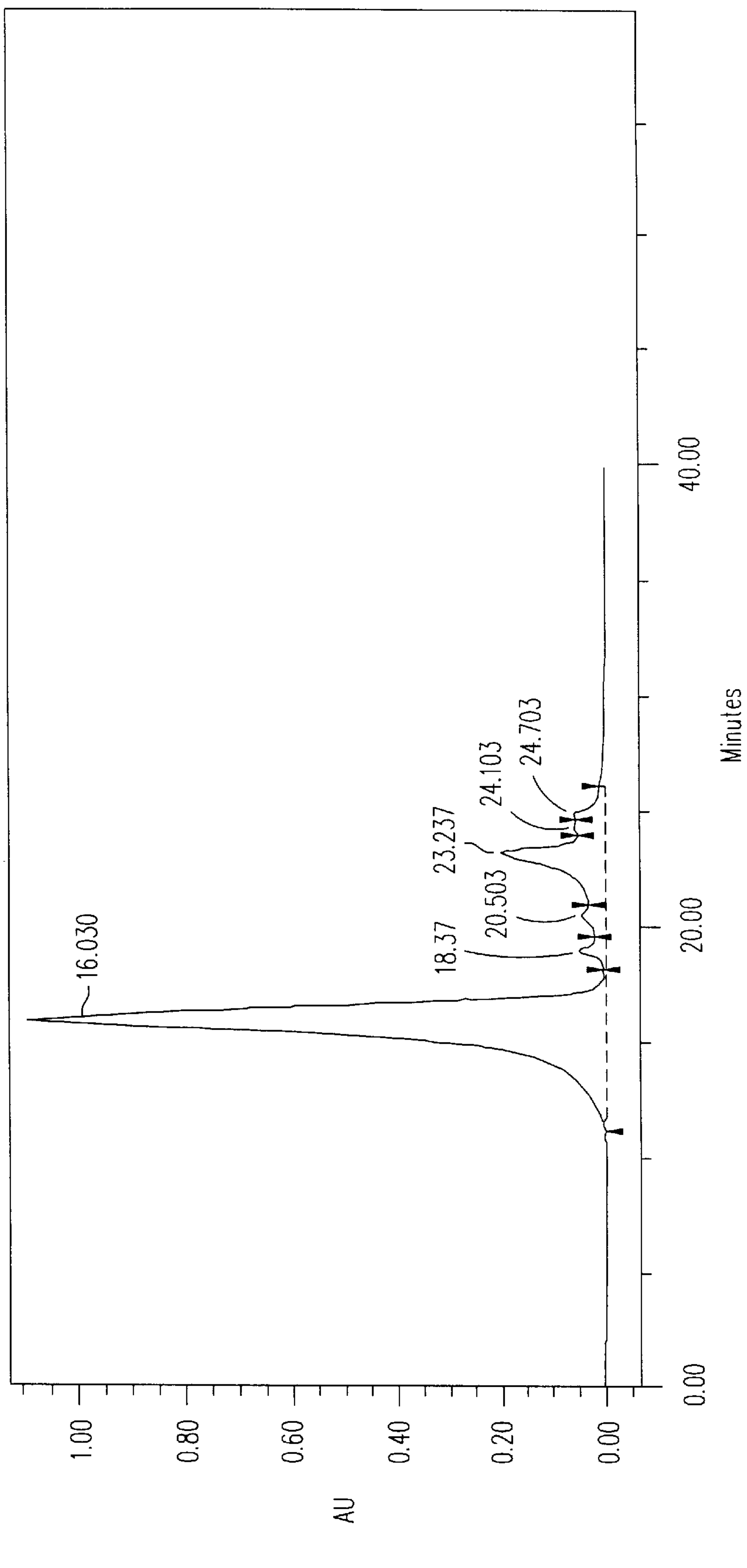
FIG. 10 is an HPLC profile of current clinical grade CM101 further subjected to HIC chromatography.

The CM101 obtained by the method of the present invention is improved over the current clinical grade CM101. Particularly, the HPLC elution profile of FIG. 10 as compared with FIG. 7*a* illustrates higher purity in the sample produced according to the present invention. FIG. 7*a* shows one narrow and symmetric main peak, instead of several peaks.

Figure 11:
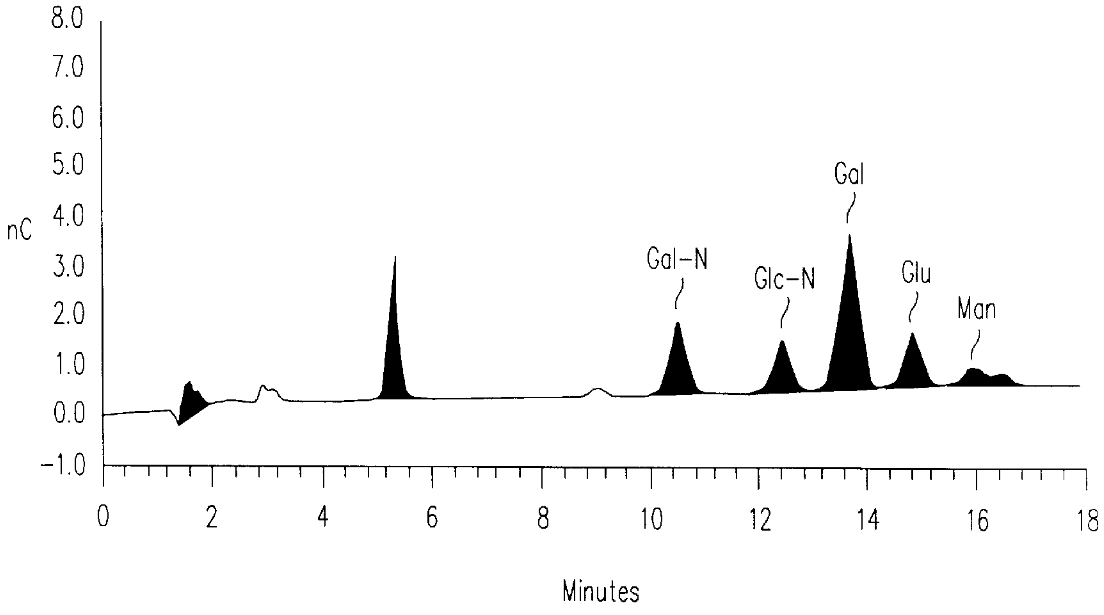
FIG. 11 illustrates a sugar analysis of a sample of current clinical grade CM101 which was further purified by HIC and HPLC.

To further demonstrate the advantageous use of the HIC column and to provide further evidence of purification of the toxin known as CM101, current clinical grade CM101 was subjected to an HIC column and HPLC purification and a sugar analysis was performed. The results, in FIG. 11, may be compared to FIG. 9. The sugar analysis shows quantitatively and qualitatively similar end products. This result is borne out in Table 3, as well.

TABLE 3

Carbohydrate Composition of CM101 (Presented as Integral Carbohydrate Ratios)

| Sugar | CM101 Purified With Present Method | Current Clinical Grade CM101 | Current Clinical Grade CM101 Further Purified |
|---|---|---|---|
| Rhamnose | 0 | 3 | 0 |
| Mannose | 1 | 3 | 1 |
| Galactose | 3 | 24 | 3 |
| Glucose | 1 | 7 | 1 |
| Glucosamine* | 1 | 13 | 1 |
| Galactosamine* | 1 | 5 | 1 |

*Present as "N-acetyl-glucosamine and N-acetyl-galactosamine", respectively, in the native polysaccharide.

Thus, the method of the present invention provides an improved method of purification which minimizes the difficulty of hazardous steps and provides excellent purity. Additionally, the product produced by the method taught herein is improved over the currently available CM101.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method of purifying a polysaccharide toxin from group B β-hemolytic Streptococcus (GBS) bacteria, which method comprises:

(a) contacting an aqueous mixture containing the toxin with a hydrophobic interaction chromatography (HIC) resin; and (b) separating the toxin from the HIC resin.

2. The method of claim 1, wherein the purity of the toxin resulting from the HIC resin contacting step is increased approximately 100–500 fold relative to the purity of the toxin in the aqueous mixture.

3. The method of claim 1, wherein the toxin resulting from the step of separating the toxin from the HIC resin is greater than 40% pure.

4. The method of claim 1, further comprising extracting the toxin of step (b) with an aqueous phenol mixture to form an aqueous phase including the toxin.

5. The method of claim 4, wherein the toxin resulting from the step of extracting the toxin with an aqueous phenol mixture is at least approximately 60% pure.

6. The method of claim 5, wherein the toxin resulting from the step of extracting the toxin with an aqueous phenol mixture is at least approximately 90% pure.

7. The method of claim 4, wherein the toxin resulting from the step of extracting the toxin with an aqueous phenol mixture is at least approximately 60% pure.

8. The method of claim 7, wherein the toxin resulting from the step of extracting the toxin with an aqueous phenol mixture is at least approximately 90% pure.

9. The method of claim 1, wherein the HIC resin further comprises a resin having hydrophobic groups selected from the group consisting of alkyl, alkoxy, and aryl groups.

10. The method of claim 9, wherein the hydrophobic groups are alkyl groups having in the range of 2 to 12 carbons.

11. The method of claim 10, wherein the hydrophobic groups are butyl groups.

12. The method of claim 11, wherein the hydrophobic groups are normal butyl groups.

13. The method of claim 9, wherein the hydrophobic groups are phenyl groups.

14. The method of claim 1, further comprising:

(c) contacting the toxin from step (b) with an ion-exchange resin; and (d) separating the toxin from the ion-exchange resin.

15. The method of claim 14, wherein the toxin resulting from the step of separating the toxin from the ion-exchange resin is at least approximately 60% pure.

16. The method of claim 15, wherein the toxin resulting from the step of separating the toxin from the ion-exchange resin is at least approximately 90% pure.

17. The method of claim 1, further comprising after the step of separating the toxin from the HIC resin:

(c) extracting the toxin with an aqueous phenol mixture to form an aqueous phase including the toxin, (d) contacting the toxin of step (c) with an ion-exchange resin; and (e) separating the toxin from the ion-exchange resin.

18. A method of purifying a polysaccharide toxin from group B β-hemolytic Streptococcus (GBS) bacteria comprising:

(1) applying a source of GBS bacterial toxin to a hydrophic interaction chromatography (HIC) column, (2) eluting the HIC column to obtain an HIC eluate including the toxin, (3) extracting the HIC eluate with a combination of phenol and an aqueous solution to form an aqueous phase including the toxin, (4) applying the aqueous phase to an ion exchange column, and (5) eluting the ion exchange column to obtain an ion exchange eluate, wherein the ion exchange eluate comprises a substantially pure toxin.

19. The method of claim 18 wherein the substantially pure toxin is CM101.

20. The method of claim 18 wherein the substantially pure toxin is at least approximately 60% pure.

21. The method of claim 20 wherein the substantially pure toxin is at least approximately 95% pure.

* * * * *